(12) United States Patent
Trivedi et al.

(10) Patent No.: US 8,617,523 B2
(45) Date of Patent: Dec. 31, 2013

(54) ANTI-BIOFILM CARBONATE COMPOUNDS FOR USE IN ORAL CARE COMPOSITIONS

(75) Inventors: Harsh M. Trivedi, Somerset, NJ (US); Tao Xu, Newton, MA (US); Davide Miksa, Doylestown, PA (US)

(73) Assignee: Colgate-Palmolive Company, New York, NY (US)

( * ) Notice: Subject to any disclaimer, the term of this patent is extended or adjusted under 35 U.S.C. 154(b) by 187 days.

(21) Appl. No.: 13/260,920

(22) PCT Filed: Apr. 1, 2009

(86) PCT No.: PCT/US2009/039140
§ 371 (c)(1),
(2), (4) Date: Sep. 29, 2011

(87) PCT Pub. No.: WO2010/114533
PCT Pub. Date: Oct. 7, 2010

(65) Prior Publication Data
US 2012/0020896 A1     Jan. 26, 2012

(51) Int. Cl.
*A61K 8/00* (2006.01)

(52) U.S. Cl.
USPC .......................................................... 424/49

(58) Field of Classification Search
USPC .......................................................... 424/49
See application file for complete search history.

(56) References Cited

U.S. PATENT DOCUMENTS

| | | |
|---|---|---|
| 3,538,230 A | 11/1970 | Pader et al. |
| 4,358,437 A | 11/1982 | Duke |
| 5,288,480 A | 2/1994 | Gaffar et al. |
| 5,578,295 A | 11/1996 | Francis et al. |
| 5,703,123 A | 12/1997 | Pelzer et al. |
| 7,005,225 B2 | 2/2006 | Qian et al. |
| 7,005,255 B2 | 2/2006 | Kaddurah-Daouk et al. |
| 7,329,489 B2 | 2/2008 | Kaddurah-Daouk et al. |
| 7,550,258 B2 | 6/2009 | Kaddurah-Daouk et al. |
| 7,635,556 B2 | 12/2009 | Kaddurah-Daouk et al. |
| 2004/0224876 A1 | 11/2004 | Jost-Price et al. |
| 2005/0014132 A1 | 1/2005 | Kaddurah-Daouk et al. |
| 2005/0113345 A1 | 5/2005 | Chow et al. |
| 2006/0134676 A1 | 6/2006 | Kaddurah-Daouk et al. |
| 2006/0134677 A1 | 6/2006 | Kaddurah-Daouk et al. |
| 2006/0134678 A1 | 6/2006 | Kaddurah-Daouk et al. |
| 2006/0141421 A1 | 6/2006 | Braunecker et al. |
| 2007/0072203 A1 | 3/2007 | Kaddurah-Daouk et al. |
| 2007/0160544 A1 | 7/2007 | Sreenivasan |
| 2008/0027146 A1 | 1/2008 | Fiorellini et al. |
| 2008/0161394 A1 | 7/2008 | Fouron et al. |

FOREIGN PATENT DOCUMENTS

| | | |
|---|---|---|
| EP | 0528468 | 2/1993 |
| EP | 1057809 | 12/2000 |
| EP | 1210928 | 6/2002 |
| EP | 1925292 | 5/2008 |
| GB | 2401865 | 11/2004 |
| WO | WO 95/13094 | 5/1995 |
| WO | WO 97/47282 | 12/1997 |
| WO | WO 01/48481 | 7/2001 |
| WO | WO 01/55386 | 8/2001 |
| WO | WO 01/85116 | 11/2001 |
| WO | WO 2005/039504 | 5/2005 |
| WO | WO 2005/057222 | 6/2005 |
| WO | WO 2005/103071 | 11/2005 |
| WO | WO 2008/093072 | 7/2008 |
| WO | WO 2009/048841 | 4/2009 |

OTHER PUBLICATIONS

Gallegos Olea et al., 2002, "Organic Carbonate from *Caloptropis procera* Leaves," Fitoterapia 73(3):263-265.
International Search Report and Written Opinion in International Application No. PCT/US09/039140 mailed Nov. 27, 2009.
Morisseau et al., 1999, "Potent Urea and Carbamate Inhibitors of Solble Epoxide Hydrolases," PNAS 96(16):8849-8854.
Belikov, 1993, Pharmaceutical Chemistry, Moskow High School, pp. 43-47.
Afflitto et al., 1989, "Salivary and plaque triclosan levels after brushing with a 0.3% triclosan/copolymer/NaF dentifrice," Amer. J. Dent. 2:207-210.
Akalin et al., 2007, "Lipid Peroxidation Levels and Total Oxidant Status in Serum, Saliva and Gingival Crevicular Fluid in Patients with Chronic Periodontitis," J. Clin. Periodontol, 34(7):558-265.

(Continued)

*Primary Examiner* — Raymond Henley, III
(74) *Attorney, Agent, or Firm* — Howard C. Lee

(57) ABSTRACT

The present invention includes oral care compositions and methods for inhibiting growth and formation of oral biofilms by quorum sensing inhibition and/or bactericidal activity. In some embodiments, the present invention discloses an oral care composition including a therapeutically effective amount of at least one carbonate compound of Formula (1) and at least one excipient: wherein, $R_1$ and $R_2$ are independently: an aliphatic radical; a hydroxyaliphatic radical; or an aryl radical. In some embodiments, the present invention discloses a method of providing oral care benefits including applying to an oral cavity an oral care composition containing a therapeutically effective amount of at least one carbonate compound of Formula (1) and at least one excipient. In some embodiments, the present invention discloses a method of up-regulating or down-regulating periodontal disease metabolites including applying to an oral cavity an oral care composition containing a therapeutically effective amount of at least on carbonate compound of Formula (1) and at least one excipient.

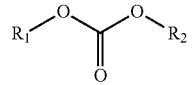

Formula 1

22 Claims, No Drawings

(56) References Cited

OTHER PUBLICATIONS

Armitage, 2004, "Analysis of Gingival Crevice Fluid and Risk of Progression of Periodontitis," Periodontol. 34:109-119.

Back et al., 2007, "Increased Leukotriene Concentrations in Gingival Crevicular Fluid from Subjects with Periodontal Disease and Atherosclerosis," Atherosclerosis 193(2):389-394.

Bergamini et al., 2004, "Oxygen, Reactive Oxygen Species and Tissue Damage," Curr. Pharm. Des. 10(14):1611-1626.

Berry et al., 2004, "Xanthine Oxidoreductase and Cardiovascular Disease: Molecular Mechanisms and Pathophysiological Implications," J. Physiol. 555(Pt. 3):589-606.

Bodet et al., 2005, "Modulation of cytokine production by *Porphyromonas gingivalis* in a macrophage and epithelial cell co-culture, model," Microbes & Infect. 7(3):448-456.

Brantzaeg et al., 1992, "Compartmentalization of lipopolysaccharide production correlates with clinical presentation in meningococcal disease," J. Infect. Dis. 166(3):650-652.

Bunnell et al.. 2000, "A lipid A analog, E5531, blocks the endotoxin response in human volunteers with experimental endotoxemia," Crit. Care Med. 28(8):2713-2720.

Cannon et al,, 2008, "Salivary Metabonomics: A New Objective Measure in Oral Care," Poster 14, 8th European Symposium on Saliva, May 14-17, 2008, The Netherlands.

Chapple et al., 2002, "Glutathione in Gingival Crevicular Fluid and Its Relation to Local Antioxidant Capacity in Periodontal Health and Disease," Mol. Pathol. 55(6):367-373.

Ciantar et al., 2002, "Development of an in vitro Microassay for Glucose Quantification in Submicrolitre Volumes of Biological Fluid," J. Periodontal Res. 37(2):79-85.

El Moudni et al., 1995, "Purification and characterisation of a metallopeptidase of *Candida albicans*," J. Med. Microbiol, 43(4):282-288.

Embery et al., 1994, "Gingival Crevicular Fluid: Biomarkers of Periodontal Tissue Activity," Adv. Dent. Res. 8(2):329-336.

Fokkema et al., 2003, "Monocyte-derived RANTES is intrinsically elevated in periodontal disease while MCP-1 levels are related to inflammation and are inversely correlated with IL-12 levels," Clin. & Exp. Immunol. 131(3):477-483.

Fothergill et al., 1977, "Catabolism of L-Lysine by *Pseudomonas aureuginosa*," J. Gen. Micriobiol. 99(1):139-155.

Gaspersic et al., 2010, "Anti-NGF treatment reduces bone resorption in periodontitis," J. Dental Res. 89(5):515-520.

Golub et al., 1998, "Modulation of the Host Response in the Treatment of Periodontitis," Dent. Today 17(10):102-6, 108-9.

Golub et al., 1997, "A matrix metalloproteinase inhibitor reduces bone-type collagen degradation fragments and specfic collagenases in gingival crevicular fluid during adult periodontitis," Inflamm. Res. 46:310-319.

Harrison, 2004, "Physiological Roles of Xanthine Oxidoreductase," Drug Metab. Rev. 36(2):363-375.

Heasman et al., 1993, "Changes in Crevicular Fluid Levels of Interleukin-1 Beta, Leukotriene B4, Prostaglandin E2, Thromboxane B2 and Tumour Necrosis Factor Alpha in Experimental Gingivitis in Humans," J. Periodontal Res. 28(4):241-247.

Holt et al., 2001, "Dental damage, sequelae, and prevention," Western J. of Medicine 174(4):288-290.

Ilgenli et al., 2006, "Gingival Crevicular Fluid Matrix Metalloproteinase-13 Levels and Molecular Forms in Various Types of Periodontal Diseases," Oral Dis. 12(6):573-579.

Imbert et al., 2002, "Effect of matrix metalloprotease inhibitors on the 95 kDa metallopeptidase of *Candida albicans*," J. Antibicrob. Chemother. 49(6):1007-1010.

Ingman et al., 1996, "Matrix metalloproteinases and their inhibitors in gingival crevicular fluid and saliva of periodontitis patients," J. Clin. Periodontol. 23(12):1127-1132.

Ingman et al., 1994, "Multiple Forms of Gelatinases/Type IV Collagenases in Saliva and Gingival Crevicular Fluid of Periodontitis Patients," J. Clin. Periodontol. 21(1):26-31.

International Search Report and Written Opinion in International Application No. PCT/US10/029674 mailed Nov. 12, 2010.

International Search Report and Written Opinion in International Application No. PCT/US10/029670 mailed Aug. 12, 2010.

International Search Report and Written Opinion in International Application No. PCT/US09/039184 mailed Jun. 25, 2010.

International Search Report and Written Opinion in International Application No. PCT/US07/060222 mailed Aug. 2, 2007.

Ishikura et al., 2003, "Cloning of the Tannerella Forsythensis (Bacteriodes Forsythus) siaHI Gene and Purification of the Sialidase Enzyme," J. Med. Micriobiol. 52(Pt. 12):1101-1107.

Jackson et al., 2007, "The Production of Reactive Oxygen and Nitrogen Species by Skeletal Muscle," J. Appl. Physiol. 102(4):1664-1670.

Jahngen et at, 1984, "High-Performance Liquid Chromatography Analysis of Purine Nucleosides in Human Gingival Crevicular Fluid," Arch. Oral Biol. 29(8):607-610.

Kantarci et al., 2003, "Neutrophil-Mediated Tissue Injury in Periodontal Disease Pathogenesis: Findings from Localized Aggressive Periodontitis," J. Periodontol. 74(1):66-75.

Karthikeyan et al., 2007, "Gingival Crevicular Fluid and Serum Leptin: Their Relationship to Periodontal Health and Disease," J. Clin. Periodontol. 34(6):467-472.

Kiili et al., 2002, "Collagenase-2 (MMP-8) and collagenase-3 (MMP-13) in adult periodontitis: molecular forms and levels in gingival crevicular fluid and immunolocalisation in gingival tissue," J. Clin. Periodontol. 29(3):224-232; Erratum in: J. Clin. Periodontol. 2004, 31(2):149.

Lamster et al., 2007, "Analysis of Gingival Crevicular Fluid as Applied to the Diagnosis of Oral and Systemic Diseases," Ann, NY Acad. Sci. 1098:216-229.

Lamster, 1997, "Evaluation of Components of Gingival Crevicular Fluid as Diagnostic Tests," Ann. Periodontol. 2(1):123-137.

Lamster et al., 1987, "The Polyamines Putrescine, Spermidine and Spermine in Human Gingival Crevicular Fluid," Arch. Oral Biol. 32(5):329-333.

Lapp et al., 2005, "Analysis of interleukin-activated human gingival fibroblasts: modulation of chemokine responses by female hormones," J. Periodontol. 76(5):803-812.

Lawton et al., 2008, "Analysis of the Adult Human Plasma Metabolome," Pharmacogenomics 9(4):383-397.

Loos et al., 2005, "Host-Derived Diagnostic Markers for Periodontitis: Do They Exist in Gingival Crevice Fluid?" Periodontol, 39:53-72.

Lorencini et al., 2009, "Changes in MMPs and inflammatory cells in experimental gingivitis," Histol. Histopathol. 24(2):157-166.

Madianos et al., 2005, "Generation of inflammatory stimuli: how bacteria set up inflammatory responses in the gingiva," J. Clin. Periodontol. 32(Supp. 6):57-71.

Mahanonda et al., 2002, "Upregulation of co-stimulatory molecule expression and dendritic cell marker (CD83) on B cells in periodontal disease," J. Periodontal Res. 37(3):177-183.

Mantyla et al., 2003, "Gingival crevicular fluid collagenase-2 (MMP-8) test stick for chair-side monitoring of periodontitis," J. Periodontol. Res. 18(4):436-439.

McAllister et al., 2008, "Spit Tests:. Searching for Biomarkers in the Salivary Proteome," Poster 37, 8th European Symposium on Saliva, May 14-17, 2008, The Netherlands.

Modeer et al., 1996, "Triclosan reduces prostaglandin biosynthesis in human gingival fibroblasts challenged with interleukin-1 in vitro," J. Clin. Periodontol, 23(10):927-933.

Nixon et al., 2000, "Cytokine responses to treponema pectinovorum and treponema denticola in human gingival fibroblasts," Infect. & Immun. 68(9):5284-5292.

Ogawa et al., 2002, "Cell activation by Porphyromonas gingivalis lipid A molecule through Toll-like receptor 4- and myeloid differentiation factor 88-dependent signaling pathway," Int. Immunol. 14(11):1325-1332.

Ozmeric, 2004, "Advances in Periodontal Diseases Markers," Clin. Chim. Acta 343(1-2):1-16.

Pacher et al., 2006, "Therapeutic Effects of Xanthine Oxidases Inhibitors: Renaissance Half a Century after the Discovery of Allopurinol," Pharmacol. Rev. 58(1):87-114.

(56) References Cited

OTHER PUBLICATIONS

Page et al., 1991, "The role of inflammatory mediators in the pathogenesis of periodontal disease," J. Periodontol. Res. 26(3 Pt. 2):230-242.
Pihlstrom et al., 2005, "Periodontal Diseases," Lancet 366(9499):1809-1820.
Pozo et al., 2005, "Longitudinal analysis of metalloproteinases, tissue inhibitors of metalloproteinases and clinical parameters in gingival crevicular fluid from periodontitis-affected patients," J. Periodontol. Res. 40(3):199-207.
Pradeep et al., 2007, "Gingival Crevicular Fluid Levels of Neopterin in Healthy Subjects and in Patients with Different Periodontal Diseases," J. Periodontol. 78(10):1962-1967.
Prapulla et al., 2007, "Gingival Crevicular Fluid VEGF Levels in Periodontal Health and Disease," J. Periodontol. 7(9):1783-1787.
Preshaw et al., 2004, "Subantimicrobial dose doxycycline as adjunctive treatment for periodontitis. A review," J. Clin. Periodontol. 31(9):697-707.
Putnins et al., 2002, "Induction of keratinocyte growth factor 1 Expression by lipopolysaccharide is regulated by CD-14 and toll-like receptors 2 and 4," Infect. & Immun. 70(12):6541-6548.
Qin et al., 2006, "Effect of Minocycline Hydrochloride Ointment on IL-8 in Gingival Crevicular Fluid," Wuhan Daxue Xuebao [Medical Journal of Wuhan Univeristy] 27(1):75-78.
Rodier et al., 1999, "A *Candida albicans* metallopeptidase degrades constitutive proteins of extracellular matrix," FEMS Microbiol. Lett. 177(2):205-210.
Rossomando et al., 1993 "A novel method for the deecion of TNF-alpha in gingival crevicular fluid," J. Periodontol. 64(5 Suppl):445-449.
Ruwanpura et al., 2004, "Prostaglandin E2 regulates interleukin-1beta-induced matrix metalloproteinase-3 production in human gingival fibroblasts," J. Dental Res. 83(3):260-265.
Search Report from the European Patent Office for Corresponding European Patent Application No. EP 1015338 dated Aug. 3, 2010.
Segal et al., 2000, "Xanthine Oxidase Contributes to Host Defense against *Burkholderia cepacia* in the p47(phox−/−) Mouse Model of Chronic Granulomatous Disease," Infect. Immun. 68(4):2374-2378.
Seymour et al., 2007, "Relationship between Periodontal Infections and Systemic Disease," Clin. Microbiol. Infect. 13(Suppl. 4):3-10.
Smalley, 1994, "Pathogenic Mechanisms in Periodontal Disease," Adv. Dent. Res. 8(2):320-328.
Sorsa et al., 1990, "The role of gingival crevicular fluid and salivary interstitial collagenases in human periodontal diseases," Arch. Oral Biol. 35 Suppl:193S-196S.
Stevens et al., 2000, "Antibacterial Properties of Xanthine Oxidase in Human Milk," Lancet 356(9232):829-830.
Sugawara, 2003, "Host Defense Mechanisms in Oral Mucosa," Tohoku University Dental Journal 22:11-18.
Sugawara et al., 2002, "Innate immune responses in oral mucosa," J. Endotoxin Res. 8(6):465-468.
Szasz et al., 2007, "A Comparison of Arteries and Veins in Oxidative Stress: Producers, Destroyers, Function, and Disease," Exp. Biol. Med, (Maywood) 232(1):27-37.
Taba et al., 2005: "Diagnostic Biomarkers for Oral and Periodontal Diseases," Dent. Clin. North Am. 49(3):551-571.
Tatakis et al., 2005, "Etiology and pathogenesis of periodontal diseases," Dent. Clin. N. Am. 49:491-516.
Teng et al., 1992, "Gingival crevicular fluid gelantinase and its relationship to periodontal disease in human subjects," J. Periodontal Res. 27(5):544-552.
Tervahartiala et al., 2000, "The in vivo Expression of the Collagenolytic Matrix Metalloproteinases (MMP-2, -8, -13, and -14) and Matrilysin (MMP-7) in Adult and Localized Juvenile Periodontitis," J. Dental Res. 79(12):1969-1977.
Toker et al., 2006, "Effect of meloxicam on gingival crevicular fluid IL-1beta and IL1 receptor antagonist levels in subjects with chronic periodontitis, and its effects on clinical parameters," Clin. Oral Investig. 10(4):305-310.
Tsai et al., 2005, "Lipid Peroxidation: A Possible Role in the Induction and Progression of Chronic Periodontitis," J. Periodontal Res. 40(5):378-384.
Tu et al., 2009, "Cyclosporine A enhances apoptosis in gingival keratinocytes of rats and in OECM1 cells via the mitochondrial pathway," J. Periodontal Res. 44(6):767-775.
Uehara et al., 2002, "Priming of human oral epithelial cells by interferon-gamma to secrete cytokines in response to lipopolysaccharides, lipoteichoic acids and peptidoglycans," J. Med. Microbiol. 51(8):626-634.
Uehara et al., 2001, "Contrasting responses of human gingival and colonic epithelial cells to lipopolysaccharides, lipoteichoic acids and peptidoglycans in the presence of soluble CD14," Med. Microbiol. Immunol. 189(4):185-192.
Valko et al., 2007, "Free Radicals and Antioxidants in Normal Physiological Functions and Human Disease," Int. J. Biochem. Cell Biol. 39(1):44-84.
Van Dyke et al., 2003, "Resolution of inflammation: A New Paradigm for the Pathogenesis of Periodontal Diseases," J. Dent. Res. 82(2):82-90.
Wang et al., 2002, "*Porphyromonas gingivalis* lipopolysaccharide signaling in gingival fibroblasts CD14 and Toll-like receptors," Crit. Rev. Oral Biol. Med. 13(2):132-142.
Weinberg et al., 1998, "Epithelial antimicrobial peptides: review and significance for oral applications," Crit. Rev. Oral Biol. Med. 9(4):399-414.
Xu et al., 2004, "Effectiveness of a Triclosan/Copolymer Dentifrice on Microbiological and Inflammatory Parameters," Compend. Contin. Educ. Dent., Medline Database Accession No. NLM15645886.
Yang et al., 2006, "Eukaryotic Pathways for the Induction of Peptidase by Pathogenic Oral Bacteria,"D-144, http://ieg.ou.edu/ASM2006/data/papers/D_144.htm.
Yoshimura, 2004, "Recogition of Periodontopathic Bacteria by Innate Immune System," J. Japanese Soc. of Periodontol. 46:94-100.
Yoshioka et al., 2003, "Effect of hydroxamic acid-based matrix metalloproteinase inhibitors on human gingival cells and *Porphyromonas gingivalis*," J. Periodontol. 74(8):1219-1224.

ANTI-BIOFILM CARBONATE COMPOUNDS FOR USE IN ORAL CARE COMPOSITIONS

CROSS-REFERENCE TO RELATED APPLICATIONS

The present application is a national stage entry under 35 U.S.C. §371 of International Patent Application No. PCT/US2009/039140, filed Apr. 1, 2009, the entirety of which is hereby incorporated by reference.

FIELD OF THE INVENTION

The present invention relates to oral compositions comprising carbonate compounds that inhibit dental plaque and caries-associated *A. naeslundii* growth and biofilm formation.

BACKGROUND OF THE INVENTION

Caries and periodontal diseases are two of the most common chronic infectious diseases affecting humankind and are always associated with dental plaque formed as a biofilm on tooth surfaces. Dental plaque is produced by sequential attachment of a variety of bacteria, which is dependent on both the species involved and the surface composition. *Actinomyces naeslundii* (*A. naeslundii*) are Gram-positive, rod-shaped bacteria that are among the first species to occupy the oral cavity and colonize the tooth's surface. *A. naeslundii* have been implicated in periodontal disease and root caries.

Quorum sensing is a means of intercellular communication between bacterial cells that allows bacteria to control gene expression and respond to population density as a group. Bacteria occupying the oral cavity, including *A. naeslundii*, use quorum-sensing systems to regulate several physiological processes, including the incorporation of foreign DNA, acid tolerance, biofilm formation, and virulence. Thus, through quorum sensing, *A. naeslundii* can optimize their physiology to adapt to environmental stimuli and can behave as a collective, thereby resulting in better colonization of hosts, evolution as a species, and improved responses to mechanical, physical, and chemical stresses. Consequently, bacteria in biofilms have an increased resistance to antimicrobials and host defenses.

SUMMARY OF THE INVENTION

The present invention includes oral care compositions and methods for inhibiting growth and formation of oral biofilms by quorum sensing inhibition and/or bactericidal activity.

In some embodiments, the present invention discloses an oral care composition including a therapeutically effective amount of at least one carbonate compound of Formula 1 and at least one excipient:

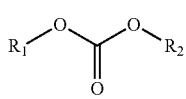

Formula 1 wherein, $R_1$ and $R_2$ are independently: an aliphatic radical; a hydroxyaliphatic radical; or an aryl radical.

In some embodiments, $R_1$ is chosen from a cyclic or branched aliphatic radical having up to 10 carbon atoms and $R_2$ is chosen from a linear or branched hydroxyaliphatic radical. In some embodiments, $R_1$ is an unsubstituted aryl radical and $R_2$ is chosen from a linear or branched hydroxyaliphatic radical having up to 10 carbon atoms.

In some embodiments, the present invention discloses a method of providing oral care benefits including applying to an oral cavity an oral care composition containing a therapeutically effective amount of at least one carbonate compound of Formula 1 and at least one excipient. In some embodiments, the oral care benefits include biofilm anti-attachment, anti-oxidant, and anti-microbial benefits.

In some embodiments, the present invention discloses a method of up-regulating or down-regulating periodontal disease metabolites including applying to an oral cavity an oral care composition containing a therapeutically effective amount of at least one carbonate compound of Formula 1 and at least one excipient. In some embodiments, the oral care composition up-regulates or down-regulates at least one member chosen from: a compound generated by amino acid metabolism; a compound generated in the urea cycle; a compound generated in glutathion conversion; a compound generated in lipid metabolism; a compound generated in carbohydrate metabolism; a compound generated by nucleic acid metabolism; vitamins; and co-factors.

DETAILED DESCRIPTION OF THE INVENTION

As used throughout, ranges are used as shorthand for describing each and every value that is within the range. Any value within the range can be selected as the terminus of the range. In addition, all references cited herein are hereby incorporated by reference in their entireties.

As used herein, the term "biofilm formation" refers to the attachment of microorganisms to surfaces and the subsequent development of multiple layers of cells.

As used herein, the term "dental plaque" refers to the diverse microbial community (predominantly bacteria) found on the tooth surface, embedded in a matrix of polymers of bacterial and salivary origin. Further, "dental plaque-associated *A. naeslundii*" refers to *A. naeslundii* that is a component of the dental plaque.

As used herein, the term "inhibition" refers to at least a decrease of dental plaque-associated bacterial (e.g., *A. naeslundii*) growth and biofilm formation.

As used herein, the term "oral care" refers to both therapeutic and prophylactic treatment of diseases and disorders affecting the oral cavity or associated medical conditions. Oral diseases and disorders include, but are not limited to: dental caries; periodontal diseases (e.g., gingivitis, adult periodontitis, early-onset periodontitis, etc.); mucosal infections (e.g., oral candidiasis, herpes simplex virus infections, recurrent aphthous ulcers, etc.); oral and pharyngeal cancers; and precancerous lesions.

As used herein, the term "quorum sensing" refers to the control of gene expression in response to cell density. Bacterial cells communicate amongst the cells of the biofilm utilizing secreted signalling molecules. Typically, gram-positive bacteria, including *A. naeslundii*, utilize small peptides as effector signalling molecules.

As used herein, the term "therapeutically effective amount" refers to a quantity of a composition high enough to provide a significant positive modification of the subject's condition(s) to be treated. A "therapeutically effective amount" as used herein includes a prophylactic amount, for example, an amount effective for preventing or protecting against dental caries and related diseases, and symptoms thereof, and amounts effective for alleviating or healing dental caries, related diseases, and symptoms thereof.

As used herein, "healthy oral status" means the absence of gingivitis and/or periodontal disease.

As used herein, "periodontal disease" means an inflammation of the periodontium including the gingival, or gum tissue; the cementum, or outer layer of the roots of teeth; the alveolar bone, or the bony sockets into which the teeth are anchored; and the periodontal ligaments which are the connective tissue fibers that run between the cementum and the alveolar bone and includes gingivitis.

The present invention includes oral care compositions and methods for inhibiting growth and formation of oral biofilms by quorum sensing inhibition and/or bactericidal activity.

I. Oral Care Compositions

In some embodiments, the present invention discloses an oral care composition for providing oral health care benefits. In some embodiments, the present invention discloses an oral care composition for providing at least one oral health care benefit selected from: oral biofilm anti-attachment, anti-oxidant, and anti-microbial benefits. In some embodiments, the present invention discloses an oral care composition for providing multiple oral health care benefits. In some embodiments, the present invention discloses an oral care composition for providing oral health care benefits including oral biofilm anti-attachment, anti-oxidant, and anti-microbial benefits.

In some embodiments, an oral care composition in accordance with the present invention up-regulates and/or down-regulates at least one periodontal disease metabolite. In some embodiments, the present invention discloses an oral care composition for up-regulating at least one periodontal disease metabolite. In some embodiments, the present invention discloses an oral care composition for down-regulating at least one periodontal disease metabolite. In some embodiments, the present invention discloses an oral care composition for up-regulating and/or down-regulating multiple periodontal disease metabolites.

In some embodiments, an oral care composition in accordance with the present invention is suitable for use in an oral cavity. In some embodiments, the oral care composition is suitable for ingestion through an oral cavity. In some embodiments, an oral care composition in accordance with the present invention includes, but is not limited to: cremes, gels, pastes, foams, emulsions, suspensions, aerosols, sprays, mouthwashes, pharmaceuticals, capsules, granules, lozenges, tablets, sweets and chewing gum. In some embodiments, the oral care composition is a dentifrice composition. In some embodiments, the dentifrice composition is a member chosen from: toothpastes, gels, mouth washes, dental floss, powders, gum adhering strips, toothbrushes, and the like. In some embodiments, the dentifrice composition in accordance with the present invention is a toothpaste.

A. Carbonate Compounds

In some embodiments, the present invention discloses an oral care composition including a therapeutically effective amount of at least one carbonate compound of Formula 1 and at least one excipient. Carbonate compounds suitable for use in the present invention conform to Formula 1:

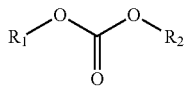

Formula 1 wherein,
$R_1$ and $R_2$ are independently: an aliphatic radical; a hydroxyaliphatic radical; or an aryl radical.

In some embodiments, an oral care composition in accordance with the present invention includes at least one carbonate compound of Formula 1, wherein $R_1$ and $R_2$ are independently: a cyclic or branched aliphatic radical; a linear or branched hydroxyaliphatic radical; or an unsubstituted aryl radical. In some embodiments, an oral care composition in accordance with the present invention includes at least one carbonate compound of Formula 1, wherein $R_1$ and $R_2$ are independently: a cyclic or branched aliphatic radical having up to 10 carbon atoms; a linear or branched hydroxyaliphathic radical having up to 10 carbon atoms; or an unsubstituted aryl radical.

In some embodiments, $R_1$ is a cyclic or branched aliphatic radical. In some embodiments, $R_1$ is a cyclic or branched aliphatic radical having up to 10 carbon atoms. In some embodiments, $R_1$ is a cyclic or branched aliphatic radical having between 5 and 10 carbon atoms. In some embodiments, $R_1$ is a cyclic or branched aliphatic radical having between 5 and 8 carbon atoms. In some embodiments, $R_1$ is an aromatic ring. In some embodiments, $R_1$ is a substituted or unsubstituted aryl radical. In some embodiments, $R_1$ is an unsubstituted aryl radical.

In some embodiments, $R_2$ is a linear or branched hydroxyaliphatic radical. In some embodiments, $R_2$ is a linear or branched hydroxyaliphatic radical having up to 10 carbon atoms. In some embodiments, $R_2$ is a linear or branched hydroxyaliphatic radical having between 6 and 10 carbon atoms.

In some embodiments, $R_1$ is chosen from a cyclic or branched aliphatic radical having up to 10 carbon atoms and $R_2$ is chosen from a linear or branched hydroxyaliphatic radical. In some embodiments, $R_1$ is an unsubstituted aryl radical and $R_2$ is chosen from a linear or branched hydroxyaliphatic radical having up to 10 carbon atoms.

In some embodiments, an oral care composition in accordance with the present invention includes at least one carbonate compound of Formula 1, wherein the at least one carbonate compound is:

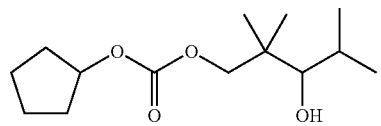 [SMILES: CC(C)C(O)C(C)(C)COC(=O)OC1CCCC1]

In some embodiments, an oral care composition in accordance with the present invention includes at least one carbonate compound of Formula 1, wherein the at least one carbonate compound is:

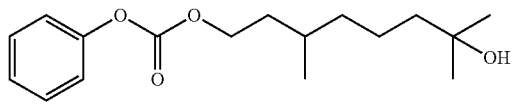 [SMILES: CC(CCCC(C)(C)O)CCOC(=O)Oc1ccccc1]

In some embodiments, an oral care composition in accordance with the present invention includes at least one carbonate compound of Formula 1, wherein the at least one carbonate compound is:

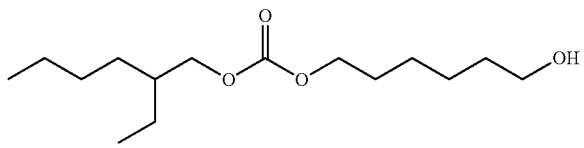 [SMILES: CCCCC(CC)COC(=O)OCCCCCCO]

In some embodiments, an oral care composition in accordance with the present invention includes the at least one carbonate compound of Formula 1 in a therapeutically effective amount of from 0.05 wt. % to 5 wt. %. In some embodiments, the at least one carbonate compound is present in an effective amount of 0.1 wt. % to 1.5 wt. %. In some embodiments, the at least one carbonate compound is present in an effective amount of 0.3 wt. % to 1.2 wt. %.

B. Excipients

In some embodiments, an oral care composition in accordance with the present invention includes at least one excipient. Excipients suitable for use in the present invention include any compound that is conventionally used in oral care compositions and that does not alter the efficacy of a carbonate compound of Formula 1.

Suitable excipients for an oral composition in accordance with the present invention may be chosen from: preservatives, abrasives (smoothing agents), further antibacterial agents, inflammation-inhibiting agents, irritation-preventing agents, irritation-inhibiting agents, further antimicrobial agents, antioxidants, binders, (mineral) fillers, buffers, carrier materials, chelating agents (chelate formers), cleaning agents, care agents, surface-active substances, emulsifiers, enzymes, foam-forming agents, foam stabilizers, foam boosters, gelling agents, gel-forming agents, bleaching agents, smell- and/or taste-modulating agents, smell- and/or taste-reducing agents, smell- and/or taste-enhancing agents, plasticizers, (mucous membrane)/skin cooling agents (cooling substances), (mucous membrane)/skin soothing agents (mucous membrane)/skin cleansing agents, (mucous membrane)/skin care agents, (mucous membrane)/skin healing agents, mucous membrane-protecting agents, stabilisers, suspending agents, vitamins, colorants, colour-protecting agents, pigments, surfactants, electrolytes, silicone derivatives, polyols, calcium carbonate, calcium hydrogen phosphate, aluminium oxide, fluorides, zinc, tin, potassium, sodium and strontium salts, pyrophosphates, hydroxyapatites.

In some embodiments, an oral care composition in accordance with the present invention includes at least one excipient, wherein the at least one excipient is chosen from: surfactants, desensitizing agents, whitening agents, tartar control agents, antibacterial agents, abrasives including silica, binders and thickening agents, detergents, adhesion agents, foam modulators, pH modifying agents, mouth-feel agents, sweeteners, flavoring agents, colorants, preservatives, combinations thereof, and the like.

1. Flavoring Agents

In some embodiments, an oral care composition in accordance with the present invention includes a flavoring agent. In some embodiments, the flavoring agent is a member chosen from: mucous membrane cooling agents, mucous membrane warming agents, sharp-tasting substances, sweeteners, sugar substitutes, organic or inorganic acidifiers (e.g., malic acid, acetic acid, citric acid, tartaric acid, phosphoric acid), bitter principles (e.g., quinine, caffeine, limonine, amarogentine, humolones, lupolones, catechols, tannins), edible mineral salts (e.g., sodium chloride, potassium chloride, magnesium chloride and sodium phosphates), essential oils (e.g., oils of spearmint, peppermint, wintergreen, sassafras, clove, sage, eucalyptus, marjoram, cinnamon, lemon, lime, grapefruit, and orange), menthol, carvone, anethole, and combinations thereof.

2. Abrasives

Abrasives suitable for use in the present invention include silica materials and particularly silica gels and precipitated amorphous silica having an oil absorption value of less than 100 cc/100 g silica and preferably in the range of from 45 cc/100 g to less than 70 cc/100 g silica. Oil absorption values are measured using the ASTM Rub-Out Method D281. Low oil absorption silica abrasives particularly useful in the practice of the present invention are marketed under the trade designation Sylodent® XWA (Davison Chemical Division of W. R. Grace & Co., Baltimore, Md. 21203). Sylodent® 650 XWA, a silica hydrogel composed of particles of colloidal silica having a water content of 29% by weight averaging from 7 to 10 microns in diameter, and an oil absorption of less than 70 cc/100 g of silica is a preferred example of a low oil absorption silica abrasive useful in the practice of the present invention. Another low oil absorption silica abrasive particularly useful in the practice of the present invention is marketed under the trade designation DP-105™ (J. M. Huber Chemicals Division, Havre de Grace, Md. 21078) is a precipitated amorphous silica having an average particle size distribution from 5 to 12 microns and an oil absorption in the range of 50 to 70 cc/100 g. Other abrasives which may be used in the practice of the present invention include precipitated silicas having a mean particle size of up to 20 microns, such as Zeodent® 115, (J. M. Huber Chemicals Division, Havre de Grace, Md. 21078), or Sylodent® 783 (Davison Chemical Division of W. R. Grace & Company), sodium metaphosphate, potassium metaphosphate, tricalcium phosphate, dihydrated dicalcium phosphate, aluminum silicate, calcined alumina, bentonite or other siliceous materials, or combinations thereof.

In some embodiments, an oral care composition in accordance with the present invention includes an abrasive excipient. In some embodiments, the abrasive excipient is a silica material. In some embodiments, the silica material is colloidal particles having an average particle size ranging from 3 microns to 12 microns. In some embodiments, the colloidal particles have an average particle size ranging from 5 to 10 microns and a pH range from 4 to 10 preferably 6 to 9 when measured as a 5 wt. % slurry. In some embodiments, the silica material is a low oil absorption silica abrasive. In some embodiments, the low oil absorption silica abrasive is present in the oral care compositions of the present invention at a concentration of 5 wt. % to 40 wt. %. In some embodiments, the low oil absorption silica abrasive is present at a concentration of 10 wt. % to 30 wt. %.

In some embodiments, the abrasive excipient is a member chosen from: silicic acids, calcium carbonates, calcium phosphates, aluminium oxides and/or hydroxyapatites, sodium metaphosphate, potassium metaphosphate, tricalcium phosphate, dihydrated dicalcium phosphate, aluminum silicate, calcined alumina, bentonite, surface-active substances (e.g., sodium lauryl sulfate, sodium lauryl sarcosinate, and cocamidopropylbetaine), and other siliceous materials, and combinations thereof.

In some embodiments, the abrasive excipient may be used individually as the sole abrasive in preparing an oral care composition of the present invention or in combination with other known dentifrice abrasives. In some embodiments, the total quantity of abrasive excipient present in the dentifrice compositions of the present invention is 5 wt. % to 60 wt. %. In some embodiments, the abrasive excipient is present in an amount of 10 wt. % to 55 wt. % by weight when the dentifrice composition is a toothpaste.

3. Anti-Microbial Agents

Anti-microbial agents suitable for use in the present invention include nonionic antibacterial agents, including halogenated diphenyl ether compounds such as 2,4,4'-trichloro-2'-hydroxydiphenyl ether (Triclosan) and 2,2'-dihydroxy-5,5'-dibromodiphenyl ether. Other useful nonionic antibacterial agents include phenolic compounds including phenol and its homologs, mono and polyalkyl and aromatic halophenols, resorcinol and its derivatives and bisphenolic compounds, such phenolic compounds being more fully disclosed in U.S. Pat. No. 5,368,844, the disclosure of which is incorporated herein by reference.

In some embodiments, an oral care composition in accordance with the present invention includes an anti-microbial agent. In some embodiments, the anti-microbial agent is a member chosen from: triclosan, chlorhexidine and its salts (e.g., its acetate, gluconate or hydrochloride), peroxides, phenols and their salts, domiphen bromide (phenododecinium bromide), bromchlorophene, Zn salts, chlorophylls, Cu salts, Cu gluconate, Cu chlorophyll, sodium lauryl sulfate, quarternary monoammonium salts such as cocoaliphaticbenzyldimethylammonium chloride or also pyridinium salts such as cetyl pyridinium chloride, and combinations thereof.

In some embodiments, the anti-microbial agent is a nonionic antibacterial agent. In some embodiments, the nonionic antibacterial agent is included in a dentifrice composition at a concentration of 0.10 wt. % to 5 wt. %. In some embodiments, the nonionic antibacterial agent is present in an amount of 0.3 wt. % to 1.2 wt. %.

4. Anti-Caries Agents

In some embodiments, an oral composition in accordance with the present invention includes an anti-caries agent. In some embodiments, the anti-caries agent is a fluoride ion source chosen from: inorganic fluoride salts, such as soluble alkali metal, alkaline earth metal salts (e.g., sodium fluoride, potassium fluoride, ammonium fluoride, calcium fluoride), a copper fluoride such as cuprous fluoride, zinc fluoride, barium fluoride, sodium fluorosilicate, ammonium fluorosilicate, sodium fluorozirconate, ammonium fluorozirconate, sodium monofluorphosphate, aluminum mono- and di-fluorophosphate, fluorinated sodium calcium pyrophosphate, and combinations thereof.

5. Dentifrice Vehicles

In some embodiments, an oral care composition in accordance with the present invention includes an orally-acceptable dentifrice vehicle. In some embodiments, the dentifrice vehicle includes a humectant therein. Humectants suitable for use in the present invention include glycerin, sorbitol, xylitol, and/or propylene glycol of molecular weight in the range of 200 to 1,000. As used herein, "sorbitol" refers to the material typically commercially available as a 70% aqueous solution. In some embodiments, the humectant concentration is from 5 wt. % to 70 wt. % of the oral composition.

In some embodiments, an oral care composition in accordance with the present invention includes water. Water employed in the preparation of commercially suitable toothpastes should preferably be deionized and free of organic impurities. In some embodiments, water is present in an amount of 15 wt. % to 30 wt. % of the oral composition. In some embodiments, water is present in an amount of 10 wt. %. In some embodiments, these amounts of water include the free water which is added in addition to that which is introduced with other materials such as with sorbitol.

6. Surfactants

Surfactants suitable for use in the compositions of the present invention include any material able to achieve increased prophylactic action and render the oral care compositions more cosmetically acceptable. The surfactant is preferably a detersive material that imparts to the oral care composition detersive and foaming properties.

In some embodiments, an oral care composition in accordance with the present invention includes a surfactant. In some embodiments, an oral care composition in accordance with the present invention includes a combination of surfactants. In some embodiments, the surfactant is an anionic surfactant including higher alkyl sulfates such as sodium lauryl sulfate. In some embodiments, the surfactant is an enzyme-compatible surfactants chosen from: nonanionic polyoxyethylene surfactants such as Pluronic® F127, Poloxamer 407, Steareth 30, Polysorbate 20; and amphoteric surfactants such as cocamidopropyl betaine and cocamidopropyl betaine lauryl glucoside. In some embodiments, an oral composition in accordance with the present invention includes a surfactant or a combination of surfactants at a total surfactant concentration in the dentifrice composition of 2 wt. % to 10 wt. %. In some embodiments, the surfactant or combination of surfactants is present in an amount of 3.5 wt. % to 6.5 wt % by weight.

7. Anti-Tartar Agents

In some embodiments, an oral care composition in accordance with the present invention includes an anti-tartar agent. In some embodiments, the anti-tartar agent is chosen from: pyrophosphate salts including dialkali or tetraalkali metal pyrophosphate salts such as $Na_4P_2O_7$, $K_4P_2O_7$, $Na_2K_2P_2O_7$, $Na_2H_2P_2O_7$ and $K_2H_2P_2O_7$, sodium tripolyphosphate; long chain polyphosphates such as sodium hexametaphosphate; and cyclic phosphates such as sodium trimetaphosphate. In some embodiments, an anti-tartar agent is present in a dentifrice composition of the present invention at a concentration of 1 wt. % to 5 wt. %.

8. Thickening Agents

In some embodiments, an oral care composition in accordance with the present invention includes a thickening agent. In some embodiments, the thickener is selected from the group consisting of, but not limited to: calcium carbonate, titanium dioxide, silicon dioxide, talcum, aluminium oxide, dicalcium phosphate, tricalcium phosphate, magnesium hydroxide, cellulose thickeners such as carboxymethyl cellulose, hyroxyalkyl celluloses such as hydroxypropyl cellulose hydroxyethyl cellulose, gums such as xanthan gum, polyglycols and polyethylene glycol, inorganic thickeners (e.g., amorphous silica compounds, natural and synthetic clays, lithium magnesium silicate and magnesium aluminum silicate), and combinations thereof.

In some embodiments, the thickening agent is an organic thickener chosen from: natural and synthetic gums and colloids including cellulose thickeners such as carboxymethyl cellulose; hyroxyalkyl celluloses such as hydroxypropyl cellulose hydroxyethyl cellulose; gums such as xanthan gum; polyglycols of varying molecular weights sold under the tradename Polyox™; and polyethylene glycol. In some embodiments, the thickening agent is an inorganic thickener chosen from: amorphous silica compounds such as colloidal silicas compounds available under the trade designation Cab-o-Sil® (manufactured by Cabot Corporation and distributed by Lenape Chemical, Bound Brook, N.J.); Zeodent® 165 (J.M. Huber Chemicals Division, Havre de Grace, Md. 21078); Sylodent® 15 (Davison Chemical Division of W.R. Grace Corporation, Baltimore, Md. 21203); natural and synthetic clays; lithium magnesium silicate (Laponite); and magnesium aluminum silicate (Veegum). In some embodiments, the thickening agent is present in a dentifrice composition of the present invention in amounts of 0.1 wt. % to 10 wt. %. In some embodiments, the thickening agent is present in an amount of 0.5 wt. % to 4.0 wt. %.

9. Anti-Oxidants

In some embodiments, an oral composition in accordance with the present invention includes an anti-oxidant. In some embodiments, the anti-oxidant is chosen from: naturally occurring tocopherols and their derivatives (e.g., Vitamin E acetate), Vitamin C and its salts and derivatives (e.g., ascorbyl palmitate, Mg ascorbyl phosphate, ascorbyl acetate), Vitamin A and derivatives (Vitamin A palmitate), tocotrienols, flavonoids, alpha-hydroxy acids (e.g., citric acid, lactic acid, malic acid, tartaric acid) and their Na, Ka and Ca salts, flavonoids, quercetin, phenolic benzylamines, propyl gallate, octyl gallate, dodecyl gallate, butylhydroxyanisole (BHA, E320), butylhydroxytoluene (BHT, 2,6-di-tert.-butyl-4-methylphenol, E321), lecithins, mono- and diglycerides of edible fatty acids esterified with citric acid, carotenoids, carotenes (e.g., α-carotene, β-carotene, lycopene) and their derivatives, phytic acid, lactoferrin, EDTA, EGTA), folic acid and its derivatives, ubiquinone and ubiquinol and their derivatives, ferulic acid and its derivatives, zinc and its derivatives (e.g., ZnO, $ZnSO_4$), selenium and its derivatives (e.g., selenium methionine), orthophosphates and Na, K and Ca salts of mono-phosphoric acids, and constituents, extracts and fractions thereof isolated from plants, (e.g., tea, green tea, algae, grapeseeds, wheat germ, camomile, rosemary, oregano), and combinations thereof.

II. Methods of Providing Oral Care Benefits

In some embodiments, the present invention discloses a method of providing oral care benefits including applying to an oral cavity an oral composition containing a therapeutically effective amount of at least one carbonate compound of Formula 1 and at least one excipient. In some embodiments, the oral care benefits include biofilm anti-attachment, anti-oxidant, and anti-microbial benefits. In some embodiments, a method of providing oral care benefits includes applying to an oral cavity an oral composition including a therapeutically effective amount of at least one carbonate compound of Formula 1 and at least one excipient as previously discussed in the above sections.

A. Oral Biofilm Anti-Attachment

Oral biofilms—comprising bacteria, bacterial extracellular byproducts, proteins, lipids, and glycolipids—are matrices formed on oral surfaces that provide loci for calculus or tartar formation.

In some embodiments, the present invention discloses a method for providing an oral biofilm anti-attachment benefit. In some embodiments, the oral biofilm anti-attachment benefit provided includes quorum sensing inhibition by a carbonate compound of Formula 1. In some embodiments, the oral biofilm anti-attachment benefit provided includes a carbonate compound of Formula 1 interacting with oral bacteria to disable it from attaching to an oral surface. In some embodiments, a carbonate compound of Formula 1 interacts with adhesins, ligands, or other moieties on the surface of oral bacteria that would ordinarily facilitate a linkage with a receptor or other moiety on the oral surface. In some embodiments, the oral biofilm anti-attachment benefit provided includes a carbonate compound of Formula 1 interacting with an oral surface to form a protective layer, such that the bacteria and biofilm components cannot adhere to the oral or tooth surface, thereby preventing an initial anchoring layer from forming on the oral surface. In some embodiments, a carbonate compound of Formula 1 may substantially cover an oral surface, and prevent attachment of the bacteria and other components of the biofilm matrix.

The oral biofilm anti-attachment benefit of the oral compositions including a therapeutically effective amount of at least one carbonate compound of the present invention was investigated using the crystal violet assay (SOP No. ATO-5345-00) in a 384-well plate over a 0.0004-2500 ppm concentration range.

B. Anti-Oxidant

Oxidation is a chemical reaction that transfers electrons from a substance to an oxidizing agent and may produce free radicals that initiate tissue-damaging chain reactions and inflammation. Oxidative stress is the result of an imbalance between the production of reactive oxygen and a biological system's ability to readily detoxify the reactive intermediates or repair the resulting damage, and may be an important factor in many disease states. Antioxidants are reducing agents capable of slowing or preventing the oxidation of other molecules.

In some embodiments, the present invention discloses a method for providing an anti-oxidant benefit. In some embodiments, the anti-oxidant benefit provided includes a carbonate compound of Formula 1 terminating a free radical chain reaction. In some embodiments, a carbonate compound of Formula 1 removes free radical intermediates. In some embodiments, a carbonate compound of Formula 1 inhibits other oxidation reactions by being oxidized itself without generating a free radical. In some embodiments, a carbonate compound of Formula 1 provides an anti-oxidant benefit efficacy comparable to existing anti-oxidants. In some embodiments, a carbonate compound of Formula 1 provides an anti-oxidant benefit efficacy comparable to Vitamin E.

The anti-oxidant activity was determined using the lipid peroxidases assay (Kamiaya Biomedical Co., Seattle, Wash.) which is a colorimetric method that measures reduction of cumene hydroperoxide radicals.

C. Anti-Microbial

In some embodiments, the present invention discloses a method for providing an anti-microbial benefit. In some embodiments, the anti-microbial benefit provided includes a carbonate compound of Formula 1 perturbing the lipid fraction of microorganism plasma membrane. In some embodiments, a carbonate compound of Formula 1 alters microbial membrane permeability resulting in leakage of intracellular materials and cell death. In some embodiments, a carbonate compound of Formula 1 crosses microbial cell membranes, penetrating into the interior of the cell and interacting with intracellular sites critical for antimicrobial activity. In some embodiments, the anti-microbial benefit provided includes a carbonate compound of Formula 1 inhibiting the formation of an oral biofilm.

The anti-microbial test was measured according to the SOP No. ATO-5308-00 for determination of Minimal Inhibitory Concenctration (MIC).

III. Methods of Regulating Periodontal Disease Metabolites

Periodontal disease metabolites in gingival crevicular fluid correspond to healthy and/or periodontal disease oral status and allow differential diagnosis of oral health. Periodontal disease metabolites may be chosen from: a compound generated by amino acid metabolism; a compound generated in the urea cycle; a compound generated in glutathion conversion; a compound generated in lipid metabolism; a compound generated in carbohydrate metabolism; a compound generated by nucleic acid metabolism; vitamins; and co-factors.

The periodontal disease metabolites described herein were discovered using metabolomic profiling techniques. Such metabolomic profiling techniques are described in U.S. Pat. Nos. 7,005,225 and 7,329,489; and U.S. patent application Ser. Nos. 11/357,732; 11/301,077 (Publication No. 2006/0134676); 11/301,078 (Publication No. 2006/0134677); 11/301,079 (Publication No. 2006/0134678) and 11/405,033 (Publication No. 2007/0072203); the entire contents of which are hereby incorporated by reference.

In some embodiments, the present invention discloses methods of up-regulating or down-regulating periodontal disease metabolites including applying to an oral cavity an oral care composition containing a therapeutically effective amount of at least one carbonate compound of Formula 1 and at least one excipient. In some embodiments, the up-regulated or down-regulated metabolite is at least one compound chosen from: a compound generated by amino acid metabolism, a compound generated in urea cycle; a compound generated in glutathion conversion; a compound generated in lipid metabolism; a compound generated in carbohydrate metabolism; a compound generated by nucleic acid metabolism; vitamins; and co-factors.

A. Up-Regulation

In some embodiments, the present invention discloses a method for up-regulating periodontal disease metabolites. In some embodiments, the method for up-regulating periodontal disease metabolites includes applying to an oral cavity an oral care composition containing a therapeutically effective amount of at least one carbonate compound of Formula 1 and at least one excipient. In some embodiments, the method of up-regulating periodontal disease metabolites includes applying to an oral cavity an oral composition including a therapeutically effective amount of at least one carbonate compound of Formula 1 and at least one excipient as previously discussed in the above sections. In some embodiments, the oral care composition up-regulates at least one metabolite selected from the radical consisting of: uric acid, reduced glutathione, oxidized glutathion, ascorbic acid, and glutamine.

B. Down-Regulation

In some embodiments, the present invention discloses a method for down-regulating periodontal disease metabolites. In some embodiments, the method for down-regulating periodontal disease metabolites includes applying to an oral cavity an oral care composition containing a therapeutically effective amount of at least one carbonate compound of Formula 1 and at least one excipient. In some embodiments, the method of down-regulating periodontal disease metabolites includes applying to an oral cavity an oral composition including a therapeutically effective amount of at least one carbonate compound of Formula 1 and at least one excipient as previously discussed in the above sections. In some embodiments, the oral care composition down-regulates at least one metabolite selected from the radical consisting of: inosine, hypoxanthine, guanosine, guanine, leucine, isoleucine, lysine, methionine, phenylalanine, proline, serine, threonine, tryptophan, tyrosine, valine, phenylacetic acid, α-hydroxyioscaproic acid, 5-amino valeric acid, choline, glycerol-3-phosphate, and N-acetylneuraminic acid.

EXAMPLES

Example 1

TABLE 1

Summary of structural information and anti-biofilm/bactericidal activity for a set of three compounds containing a carbonate moiety.

| Compounds | Molecular Weight | MBEC[1] (ppm)* | MIC[2] (ppm)* |
|---|---|---|---|
| Compound 58 | 258.35 | 156 | 625 |
| Compound 59 | 294.39 | 78 | 156 |
| Compound 60 | 274.4 | 39 | 78 |

[1]MBEC = Minimum Biofilm Eradication Concentration (anti-biofilm)
[2]MIC = Minimum Inhibitory Concentration (bactericidal)
*Based on a single species of *A. naeslundii* biofilm Example 2

The carbonate compounds of the present invention formulated in a toothpaste may have the ability to up-regulate or down-regulate at least one member chosen from: a compound generated by amino acid metabolism; a compound generated in the urea cycle; a compound generated in glutathion conversion; a compound generated in lipid metabolism; a compound generated in carbohydrate metabolism; a compound generated by nucleic acid metabolism; vitamins; and co-factors.

Compound 58

As discussed in the specification and the examples above, contacting an oral cavity with Compound 58 formulated in a toothpaste may down-regulate the production of one or more of the following metabolites: inosine, hypoxanthine, guanosine, guanine, leucine, isoleucine, lysine, methionine, phenylalanine, proline, serine, threonine, tryptophan, tyrosine, valine, phenylacetic acid, α-hydroxyioscaproic acid, 5-amino valeric acid, choline, glycerol-3-phosphate, and N-acetylneuraminic acid.

Contacting an oral cavity with Compound 58 formulated in a toothpaste may up-regulate the production of one or more of the following metabolites: uric acid, reduced glutathione, oxidized glutathion, ascorbic acid, and glutamine.

Compound 59

As discussed in the specification and the examples above, contacting an oral cavity with Compound 59 formulated in a toothpaste may down-regulate the production of one or more of the following metabolites: inosine, hypoxanthine, guanosine, guanine, leucine, isoleucine, lysine, methionine, phenylalanine, proline, serine, threonine, tryptophan, tyrosine, valine, phenylacetic acid, α-hydroxyioscaproic acid, 5-amino valeric acid, choline, glycerol-3-phosphate, and N-acetylneuraminic acid.

Contacting an oral cavity with Compound 59 formulated in a toothpaste may up-regulate the production of one or more of the following metabolites: uric acid, reduced glutathione, oxidized glutathion, ascorbic acid, and glutamine.

Compound 60

As discussed in the specification and the examples above, contacting an oral cavity with Compound 60 formulated in a toothpaste may down-regulate the production of one or more of the following metabolites: inosine, hypoxanthine, guanosine, guanine, leucine, isoleucine, lysine, methionine, phenylalanine, proline, serine, threonine, tryptophan, tyrosine, valine, phenylacetic acid, α-hydroxyioscaproic acid, 5-amino valeric acid, choline, glycerol-3-phosphate, and N-acetylneuraminic acid.

Contacting an oral cavity with Compound 60 formulated in a toothpaste may up-regulate the production of one or more of the following metabolites: uric acid, reduced glutathione, oxidized glutathion, ascorbic acid, and glutamine.

What is claimed:

1. An oral care composition comprising a therapeutically effective amount of at least one carbonate compound of Formula 1 and at least one excipient:

$$R_1\text{—O—C(=O)—O—}R_2 \quad \text{Formula 1}$$

wherein,
$R_1$ and $R_2$ are independently: an aliphatic radical; a hydroxyaliphatic radical; or an aryl radical,
and wherein the oral care composition has at least one of the following oral care benefits:
anti-microbial activity,
anti-oxidant activity,
and biofilm anti-attachment activity.

2. The oral care composition of claim 1, wherein $R_1$ and $R_2$ are independently: a cyclic or branched aliphatic radical; a linear or branched hydroxyaliphatic radical; or an unsubstituted aryl radical.

3. The oral care composition of claim 2, wherein $R_1$ and $R_2$ are independently: a cyclic or branched aliphatic radical having up to 10 carbon atoms; a linear or branched hydroxyaliphathic radical having up to 10 carbon atoms; or an unsubstituted aryl radical.

4. The oral care composition of claim 3, wherein $R_1$ is chosen from a cyclic or branched aliphatic radical having up to 10 carbon atoms.

5. The oral care composition of claim 4, wherein $R_2$ is chosen from a linear or branched hydroxyaliphatic radical.

6. The oral care composition of claim 3, wherein $R_1$ is an unsubstituted aryl radical.

7. The oral care composition of claim 6, wherein $R_2$ is a linear or branched hydroxyaliphatic radical having up to 10 carbons.

8. An oral care composition comprising a therapeutically effective amount of at least one carbonate compound of Formula 1 and at least one excipient:

$$R_1\text{—O—C(=O)—O—}R_2 \quad \text{Formula 1}$$

wherein,
$R_1$ is an aryl radical, and $R_2$ is a hydroxyaliphatic radical.

9. An oral care composition comprising a therapeutically effective amount of at least one carbonate compound of Formula 1 and at least one excipient:

$$R_1\text{—O—C(=O)—O—}R_2 \quad \text{Formula 1}$$

wherein,
$R_1$ is a branched aliphatic radical, and $R_2$ is a hydroxyaliphatic radical.

10. The oral care composition of claim 1, wherein the at least one carbonate compound of Formula 1 is:

[structure: cyclopentyl carbonate of 2,2,3-trimethyl-3-hydroxypentyl]

11. The oral care composition of claim 1, wherein the at least one carbonate compound of Formula 1 is:

[structure: phenyl carbonate of hydroxyaliphatic chain]

12. The oral care composition of claim 1, wherein the at least one carbonate compound of Formula 1 is:

[structure: 2-ethylhexyl carbonate of hydroxyhexyl]

13. The oral care composition of claim 1, wherein at least one excipient is selected from the group consisting of: surfactants, desensitizing agents, whitening agents, tartar control agents, antibacterial agents, abrasives including silica, binders and thickening agents, detergents, adhesion agents, foam modulators, pH modifying agents, mouth-feel agents, sweeteners, flavorants, colorants, preservatives, combinations thereof, and the like.

14. A method of providing oral care benefits comprising applying to an oral cavity an oral care composition containing a therapeutically effective amount of at least one carbonate compound of Formula 1 and at least one excipient:

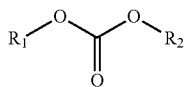

Formula 1 wherein $R_1$ and $R_2$ are independently: an aliphatic radical; a hydroxyaliphatic radical; or
an aryl radical;
and wherein the oral care benefits comprise anti-microbial activity and/or anti-oxidant activity.

15. The method of claim 14, wherein at the oral care benefits comprise biofilm anti-attachment.

16. A method of up-regulating or down-regulating periodontal disease metabolites comprising applying to an oral cavity an oral care composition containing a therapeutically effective amount of at least one carbonate compound of Formula 1 and at least one excipient:

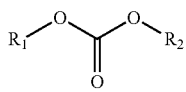

Formula 1 wherein,
$R_1$ and $R_2$ are independently: an aliphatic radical; a hydroxyaliphatic radical; or an aryl radical.

17. The method of claim 16, wherein the oral care composition up-regulates or down-regulates at least one member chosen from: a compound generated by amino acid metabolism; a compound generated in the urea cycle; a compound generated in glutathion conversion; a compound generated in lipid metabolism; a compound generated in carbohydrate metabolism; a compound generated by nucleic acid metabolism; vitamins; and co-factors.

18. The method of claim 17, wherein the oral care composition up-regulates at least one metabolite chosen from: uric acid, reduced glutathione, oxidized glutathion, ascorbic acid, and glutamine.

19. The method of claim 17, wherein the oral care composition down-regulates at least one metabolite chosen from: inosine, hypoxanthine, guanosine, guanine, leucine, isoleucine, lysine, methionine, phenylalanine, proline, serine, threonine, tryptophan, tyrosine, valine, phenylacetic acid, α-hydroxyioscaproic acid, 5-amino valeric acid, choline, glycerol-3-phosphate, and N-acetylneuraminic acid.

20. The oral care composition of claim 8, wherein the at least one carbonate compound of Formula 1 is:

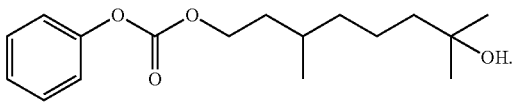 [SMILES: CC(CCCC(C)(C)O)CCOC(=O)Oc1ccccc1]

21. The oral care composition of claim 9, wherein the at least one carbonate compound of Formula 1 is:

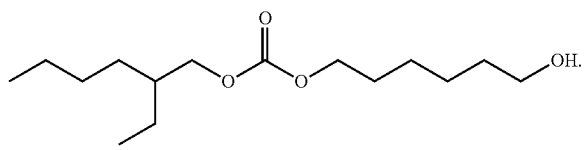 [SMILES: CCCCC(CC)COC(=O)OCCCCCCO]

22. The oral care composition of claim 8, wherein at least one excipient is selected from the group consisting of: surfactants, desensitizing agents, whitening agents, tartar control agents, antibacterial agents, abrasives including silica, binders and thickening agents, detergents, adhesion agents, foam modulators, pH modifying agents, mouth-feel agents, sweeteners, flavorants, colorants, preservatives, combinations thereof, and the like.

* * * * *